(12) United States Patent
Goldman et al.

(10) Patent No.: US 7,781,185 B2
(45) Date of Patent: Aug. 24, 2010

(54) APPARATUS AND METHOD FOR TESTING LIQUID SAMPLES

(75) Inventors: Ross Bryan Goldman, Scarborough, ME (US); David Edward Townsend, Falmouth, ME (US); Kenneth E. Smith, Saco, ME (US); Kathleen R. McCarthy, Buxton, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 493 days.

(21) Appl. No.: 11/852,540

(22) Filed: Sep. 10, 2007

(65) Prior Publication Data

US 2008/0003638 A1    Jan. 3, 2008

Related U.S. Application Data

(62) Division of application No. 10/417,763, filed on Apr. 17, 2003, now Pat. No. 7,297,531.

(51) Int. Cl.
*C12Q 1/24* (2006.01)
*C12Q 1/02* (2006.01)
*C12Q 1/04* (2006.01)

(52) U.S. Cl. .............................. 435/30; 435/29; 435/34
(58) Field of Classification Search ....................... None
See application file for complete search history.

(56) References Cited

U.S. PATENT DOCUMENTS

| 3,787,290 | A | * | 1/1974 | Kaye | ........................... 435/40 |
| 4,385,115 | A | * | 5/1983 | de Zabala et al. | ............. 435/33 |
| 5,620,895 | A | * | 4/1997 | Naqui et al. | ............. 435/288.2 |

* cited by examiner

*Primary Examiner*—Vera Afremova
(74) *Attorney, Agent, or Firm*—Carter, DeLuca, Farrell & Schmidt, LLP

(57) ABSTRACT

An article for holding a liquefied sample for the quantification of biological material in the sample includes a device having a reaction chamber enclosing a volume therein, the reaction chamber having an upper opening through which a liquefied sample can be poured and a plurality of discrete non-permeable compartments, each of the compartments having an upper rim and being configured and dimensioned to hold separate aliquots of a liquefied sample therein; and a gasket lid removably secured to the top of the device, the gasket lid being configured and dimensioned for sealing the upper rim of each compartment to prevent liquid communication between the compartments.

18 Claims, 5 Drawing Sheets

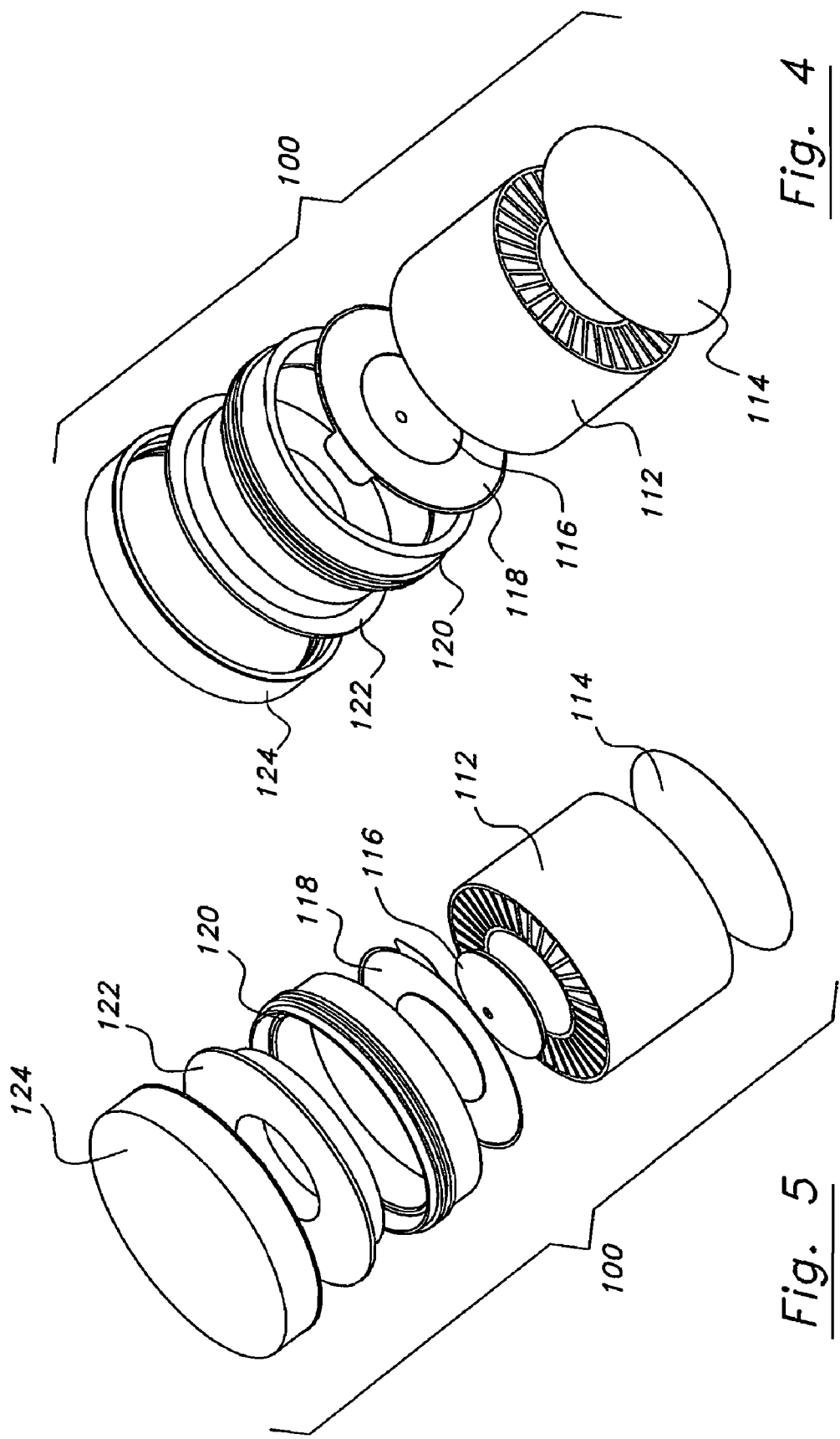

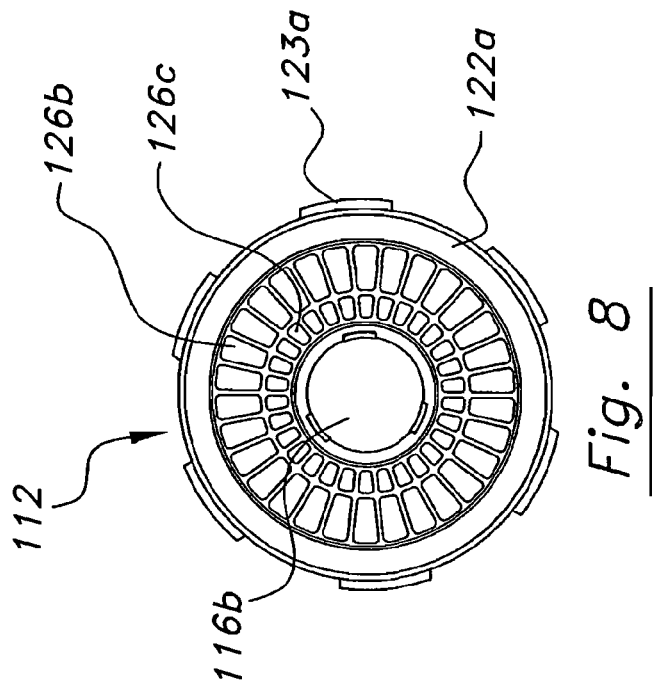
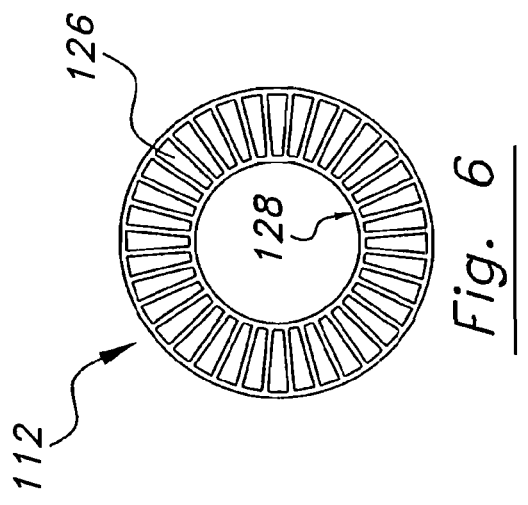
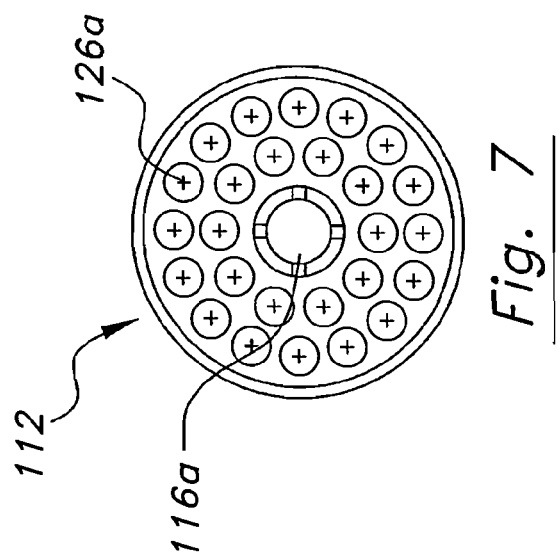

ary of the invention. The invention generally makes use of a novel article, which is designed to hold a liquefied sample in which chemical and/or microbiological reactants are provided. For example, such chemical reactants may be a specific growth medium for detecting the presence of coliforms and *E. coli*, such as the Colilert® chemical mixture discussed above or another chemical/microbiological reactants that are not based on the Defined Substrate Technology®. It may also be a specific growth medium for enterococci, such as the Enterolert™ chemical mixture (IDEXX Laboratories, Inc.). The device is designed to accept the liquefied sample to be tested and allow for the liquefied sample to be distributed throughout its internal volume, and aliquoting into separated compartments within the device. Generally, such compartments will allow separate chemical or biochemical reactions to occur in a plurality of aliquots of the liquefied sample to be tested. Such compartments will also prevent one aliquot of the liquid from affecting the reactions in another aliquot. In a simple embodiment, the invention features an article, having a gasket lid placed on the top of the device and a reaction chamber at the bottom of the device; such a reaction chamber contains at least two separate compartments, into which is introduced a liquefied sample and that the liquefied sample is distributed into the individual compartments by closing the gasket lid of the device. Each compartment then contains an aliquot of the original liquefied sample. In another embodiment, the invention features an article, having a gasket lid placed on the top of the device, a liquid overflow chamber, and a reaction chamber at the bottom of the device; such a reaction chamber contains at least two separate compartments, each compartment containing a pre-determined amount of chemical mixture, which allows the detection of the presence of biological material, into which is introduced a liquefied sample and that the liquefied sample is caused to be distributed into individual compartment by simply closing the gasket lid of the device. Each compartment then contains an aliquot of the original liquefied sample.

In general, the device is in a circular shape with a gasket lid placed in the top and in a wider end portion of the device. Upon the closure of the device, the downward compression force allows the liquefied sample to partition into each compartment and the gasket to engage in sealing action to the upper rim of each compartment, thereby isolating the liquefied sample in each compartment. This gasket alone or in combination with other features of the device must resist any internal pressures, which is generated by the activity of the biological material for up to 5 days after the device has been sealed. In a preferred embodiment, the gasket lid has both internal and external bayonet style closures, which are engaged in 1/32 to 1/2; preferably, 1/16 to 1/8, rotational turning of the lid; this creates the downward compression force of the gasket to the upper rim of each compartment, thus sealing and isolating from all other test compartments. The liquid overflow chamber in the device is adapted to accommodate any excess liquefied sample volume; preferably this overflow chamber will allow retaining 0 to 50% of the total sample volume.

In a preferred embodiment, the overflow chamber is a moat style or an annual ring style of collection area surrounding the device. In another embodiment, the overflow chamber can be located in the center of the device. In yet another embodiment, both a moat style and centrally located overflow chamber may be present in the device. There are at least two compartments in the reaction chamber. The number of compartments is configured in such a way that a desirable MPN counting range is achieved. Typically, the number of compartments is between 5 and 60 inclusive, preferably in the range of 12 and 36. In general, the compartments are substantially equal size, to hold an approximately 0.1 to 100 ml aliquot, preferably in the range of 1.5 to 20 ml aliquot; and even more preferably in the range of 2.5 ml to 5.5 ml. The compartments can be of any shapes, such as circular, triangular, rectangular, elliptical, or trapezoid, preferably, in the trapezoid shape. The trapezoidal shape may promote the entrance of the liquefied sample into the smaller truncated inside diameter, while the larger open end of the trapezoid permits unrestricted exhausting of the displaced air from within each compartment. The compartments may be arrayed in any format in the device, preferably in a circular fashion.

In yet other preferred embodiments, a first plurality of compartments is of one size (e.g. 3 ml) and a second plurality and/or a third plurality of compartments are provided of different sizes, e.g. of smaller size (e.g. 0.03 and 0.3 ml) than that of the first plurality. These embodiments have application for use when the concentration of the biological material to be quantified in the sample is high. The various sizes of compartments eliminate the needs of diluting sample, thereby saving time and possible error due to dilution, and increase the overall accuracy for the quantification.

In a related aspect, the invention features a test kit for use in the quantification of a biological material in a liquefied sample. The test kit includes an article as described above and a specific biological detection chemical mixture for detecting coliforms and E. coli or other chemical mixture for detecting enterococci. In yet another embodiment, the test kit includes an article as cited above and an appropriate, predetermined amount of specific biological detection chemical mixture in the separate compartments.

In a related aspect, the invention features a method for the quantification of a biological material in a liquefied sample. The method includes the steps of providing an article as described above and adding a testing medium to a liquefied sample, which is then added into the device. The method further includes distributing the sample into individual compartments within the device so that the mixture of the testing medium and the liquefied sample is secured in a plurality of separate aliquots within the compartments. The method then finally involves detection of the presence or absence of biological material in each compartment by any of the number of standard means, for example as described below. In a further related aspect, the invention features a method for the quantification of a biological material in a liquefied sample. The method includes the steps of providing an article with the pre-determined amount of chemical mixtures in the compartments as described above and adding a liquefied sample into the device. The method further includes distributing the liquefied sample into each individual compartment within the device so that the mixture of the testing medium and the liquefied sample is secured in a plurality of separate aliquots within the compartments. The method then finally involves detection of the presence or absence of biological material in each compartment by any of the number of standard means. The methods of this invention further include incubating the device at the desired temperature for a desired time to allow growth and detection of bacteria, or reaction of any chemical entity, within the liquefied sample and the test medium.

In preferred embodiments, the biological material to be quantified is E. coli and coliform bacteria. These aspects of the invention are applicable, however, to any biological materials to be quantified, e.g. enterococci, staphylococcus, listeriae, bacteriophages (or viruses), or protein that is present at any level in a sample, provided that one or a plurality of units of the material can be detected. The choices of a testing medium will depend on the biological material to be detected. The testing medium preferably is a medium, which will detect the presence of the biological material sought to be quantified, and substantially not detect the presence of other biological material likely to be in the sample. It should also be a material, which will cause some viable or otherwise sensible change, such as color and/or fluorescence changes, if the biological material to be detected and quantified is present in the sample.

Thus, the present invention is a novel method for the quantification of biological material in a liquefied sample. This method is much easier to use as compared to the transitional methods of MF and other MPN-based methods. Furthermore, this method does not require the use of an instrument to distribute and isolate liquefied sample in the device. Because the present invention is so easy to use, this invention has the application to serve as a sampling and quantification device simultaneously. Devices and methods of this invention do not require trained laboratory personnel to perform the assay in the laboratory setting. Instead, it can be used as a direct sampling device and allow the quantification of biological material process to take place in situ in the field. The method generally includes the following steps: adding the liquefied sample in an article designed to retain the sample, allow aliquoting into a number of separate compartments, sealing the container by closing the upper container cap and therefore distributing the sample substantially equally among a plurality of discrete non-permeable compartments in the article so that the mixture of the testing medium and sample is secured within the compartments without the risk of cross contamination; incubating the article; and recording and analyzing the results.

The present invention also features a novel article for holding the liquefied sample during the quantification method. The article includes an opening through which a liquefied sample can be poured into the article; a plurality of liquid impermeable compartments configured and arranged to separate the liquefied sample; and a passage which allows the liquefied sample to be distributed substantially evenly throughout the individual compartment of the article. The individual compartment is formed so that the liquefied mixture is partitioned into and secured into these discrete impermeable compartments.

The article and its use depend on the presence of a plurality of compartments, which can be formed so that they are essentially impermeable to the sample and the testing medium used, and to any resulting reaction product(s). The number of compartments can vary, but should be sufficient for any one sample to be analyzed with the required accuracy. In preferred embodiments, the plurality of compartments are created either by the injection mould technique or the extrusion technique. As noted above, the article of this invention may be made from any material, which can be created into liquid impermeable compartments such as, for example, PVC, polypropylene or polystyrene. The material chosen can vary depending on the substrate or the product of any chemical reaction. For example, if the presence of specific bacteria is indicated by the production of ortho-nitrophenol (ONP), a significant amount of this product should not be able to pass through the material of the article or diffuse from one compartment to the others during the quantification process.

In embodiments where different sized compartments are provided, the articles allow more accurate quantification without dilution of the liquefied sample. Thus, the advantages of such an article are that it eliminates the dilution steps thus saving time and avoiding any potential error due to dilution.

Other features and advantages of the invention will be apparent from the following description of the preferred embodiments thereof, and from the claims.

BRIEF DESCRIPTION OF THE DRAWINGS

The foregoing advantages and features of the presently disclosed apparatus and methods for liquefied sample testing will become more readily apparent and may be understood by referring to the following detailed description of illustrative embodiments, taken in conjunction with the accompanying drawings, in which:

FIG. 4 is a perspective view with parts separated from a slightly angled and bottom oriented perspective of the embodiment of FIG. 1;

FIG. 5 is a further perspective view with parts separated from a slightly angled and top oriented perspective of the embodiment of FIG. 1;

FIG. 6 is a top plan view of a container of the liquid sample testing apparatus;

FIG. 7 is a top plan view schematically illustrating an alternate arrangement of target compartments;

FIG. 8 is a top plan view schematically illustrating an alternate arrangement of target compartments with different sizes.

DETAILED DESCRIPTION OF PREFERRED EMBODIMENTS

Figure 1:
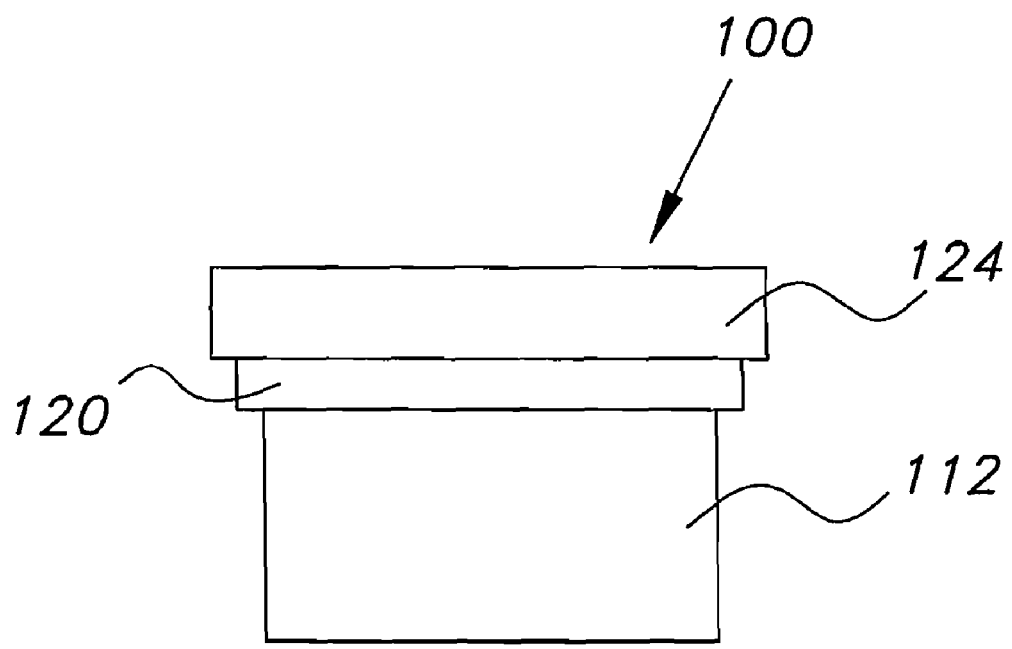
FIG. 1 is a side perspective view of one illustrative embodiment of a liquid sample testing apparatus constructed in accordance with the present disclosure.
Figure 2:
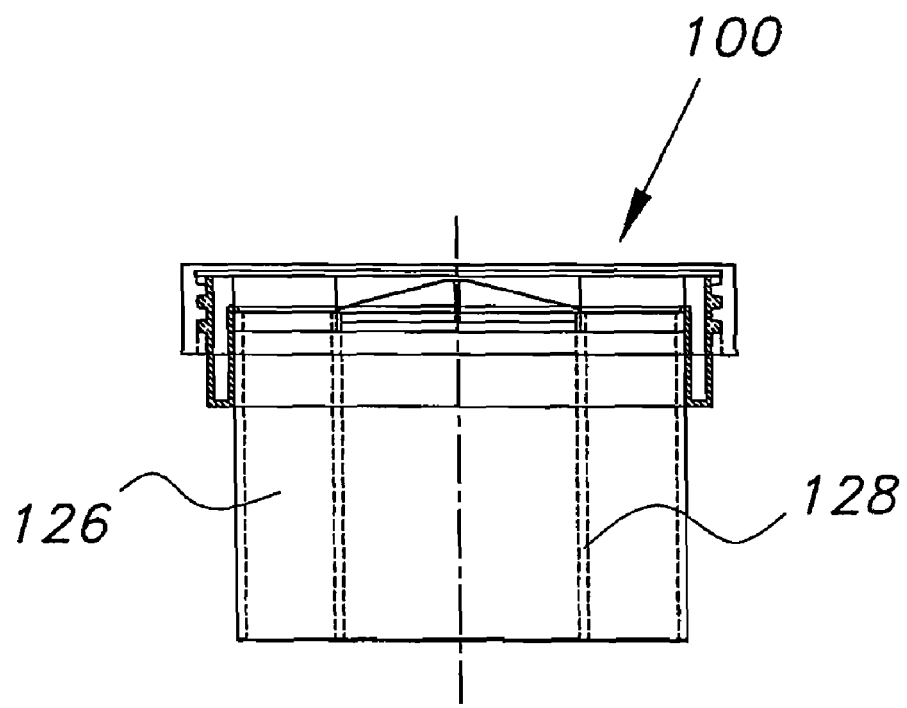
FIG. 2 is a cross-sectional view similar to FIG. 1, which shows the relative orientation of the various internal features of the embodiment of FIG. 1.

Referring now in specific detail to the drawings, in which like reference numerals identify similar or identical elements throughout the several views, the following detailed description will focus on specific exemplary embodiments of water sample testing apparatus and methods. However, it is to be understood that the apparatus and methods disclosed herein may be adapted for use in testing for presence/absence and quantification of biological material in various different types of liquefied samples as may be desired or necessary for a given application. Accordingly, the presently disclosed apparatus and methods are applicable to any biological material that is present at any level in a liquefied sample (provided that one or more units of the material can be detected), and to any applicable testing medium.

Referring now to FIGS. 1-5, one illustrative embodiment of a water testing apparatus specifically configured and adapted to achieve presence/absence indication for a targeted microorganism, for example, E. coli and coliform bacteria is shown generally as test device 100 in the form of a self-contained unit. It is contemplated, however, that the presently disclosed liquid testing apparatus and method may be adapted to test for quantification based on MPN methods.

Some of the components of test device 100 may be assembled as a sub-assembly prior to assembly of the complete unit. For example, a sub-assembly 110 of test device 100 may consist of a multi-compartmented containment member such as container 112 sealed at a bottom end by a substantially transparent or translucent closure, such as clear window 114, a fill diverter 116, an adherent seal 118, and a fill ring 120. Alternatively, a sub-assembly of the multi-compartmented chamber 110 of the test device 100 may be designed to incorporate the features of multiple components into a single unit (as shown by chamber 210 in FIG. 9); and incorporates the functions of the embodiment of FIG. 1.

Container 112 is formed from any suitable liquid impermeable material, for example PVC, polypropylene, or polystyrene by suitable techniques such as injection molding. As shown in FIGS. 3-6, container 112 is cylindrically configured having a circular array of 36 individually isolated target compartments 126 formed radially around a central cylindrical void defined by inner wall 128. The bottom end of container 112 may be sealed by way of a clear planar member such as window 114, which is sealed to the end of container 112 by suitable techniques, for example, ultrasonic welding, adhesives or other known techniques. It is envisioned that window 114 may provide readability enhancement characteristics for example magnification to provide the user with an enlarged view of the end of each test compartment 126. Alternatively, container 112 may be formed through an injection mould technique (as shown by chamber 210 in FIG. 9) with a clear closed bottom end.

Each of target compartments 126 is terminated on one end at inner wall 128, extends radially outward toward and terminates near the periphery of container 112. Target compartments 126 are configured and dimensioned to contain a predetermined amount of sample to correspond to a predetermined metered amount of medium to be mixed with the sample and incubated in each respective compartment. For example, test device 100 may be configured and dimensioned to receive a sample volume of approximately 100 ml, which when divided into each of the 36 compartments will result in approximately 2.78 ml being potentially available for each target compartment 126.

Figure 3:
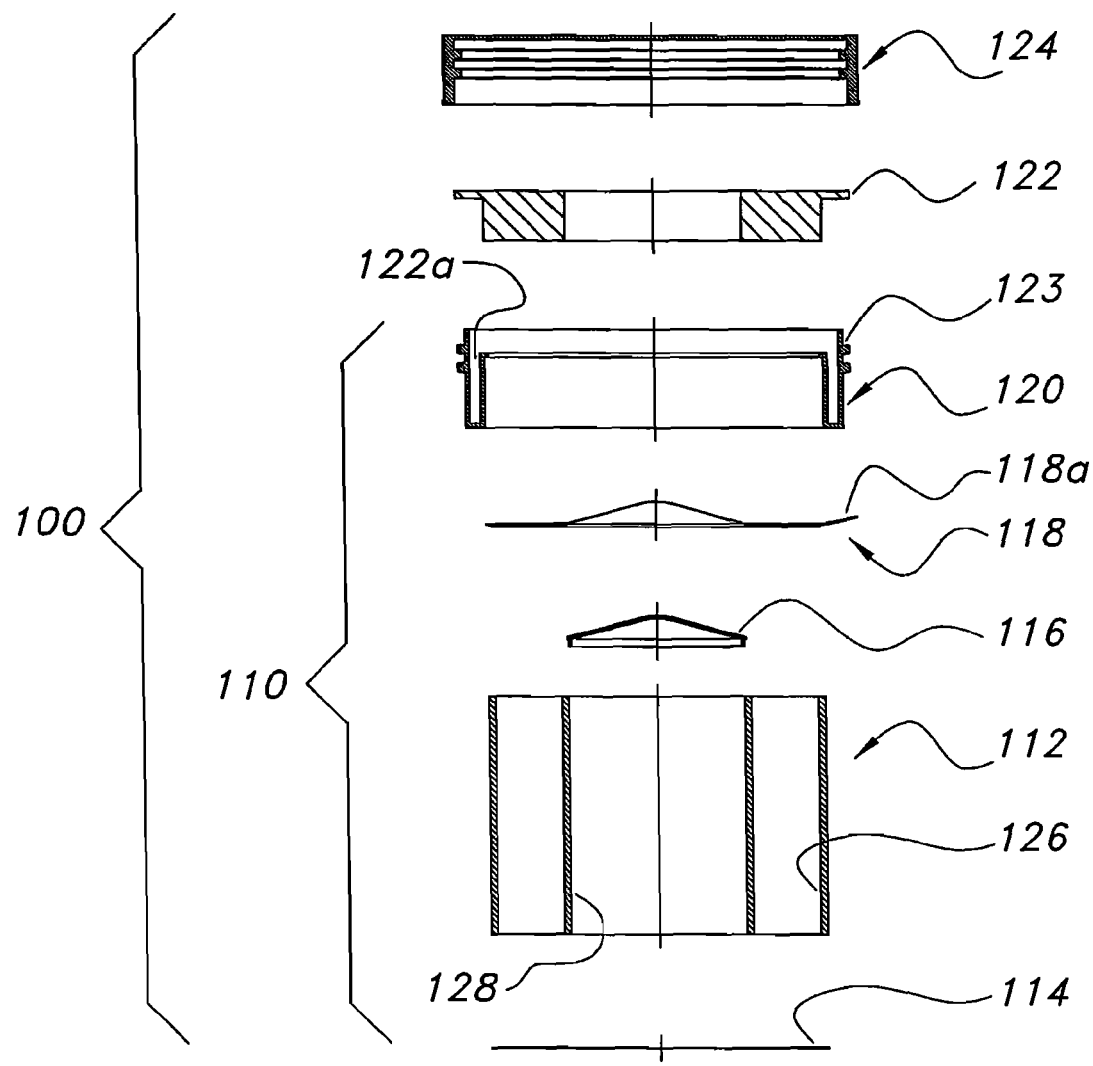
FIG. 3 is a cross-sectional view with parts separated.

As shown in FIGS. 3-5, fill diverter 116 is secured in the top open end of inner circular wall 128 by suitable attachment techniques such as friction fit, adhesives, ultrasonic welding or the like. The fill diverter 116 is secured to container 112 such that a convex surface of the diverter 116 is oriented toward the top of container 112. The convex surface of fill diverter 116 may be selected from various surface configurations, such as conical, frusto-conical, or dome-shaped. Alternatively, the fill diverters 116, 116a, and 116b (FIGS. 7 and 8)

may be provided with channels formed therein to land, to divide and direct the liquefied sample and/or sample/medium mixture toward the target compartments 126, 126a, 126b, and/or 126c.

It is also envisioned that the sample may be dispensed into target compartments 126 by a pipette array configured and dimensioned to simultaneously dispense equal volumes of sample into the respective target compartments 126.

A removable seal such as peel-able foil seal 118 may be optionally configured and dimensioned to seal the open top ends of target compartments 126 to ensure the integrity of each of individual target compartments. If needed, seal 118 is preferably secured to the open end of container 112 after the metered amounts of medium are added to provide a fluid barrier preventing contamination of the compartments and loss of medium. Seal 118 may be formed as a pressure sensitive foil seal with an extended tab portion 118a, which is readily grasped by the user to remove the seal just prior to introduction of the sample. As shown in FIGS. 3-5, seal 118 is configured and dimensioned to fit over fill diverter 116 and target compartments 126. It is envisioned that seal 118 may be formed in a washer-like configuration with an opening in the middle to fit around the perimeter of fill diverter 116.

Target compartments 126 are shown as being of uniform volume and having a cross-sectional trapezoidal shape, which is narrower nearer the center of container 112 and broader toward the outer periphery thereof. In this manner, a fluid sample poured into test device 100 is efficaciously dispensed into each of target compartments 126, as described in greater detail herein. It is also contemplated that target compartments 126 may be formed in other geometrical cross-sections, have different volumes relative to each other such as 126b and 126c (shown in FIG. 8) or include have several groups of compartments having the same volume, for example to conduct multiple tests simultaneously (multiplexing) where different tests require different target compartment volumes.

Additionally, it is envisioned that target compartments 126 may be arrayed in various patterns limited only by the spatial boundaries of the lateral cross-sectional area of container 112. For example, as shown in FIG. 7, target compartments 126a having a uniform lateral cross-section opening may be formed in an array across the surface of container 112 as schematically represented by circles having centers indicated by a "+". Target compartments 126a may be formed in any desired geometrical configuration. Various container configurations are contemplated wherein target compartments may be formed in different numbers and sizes which may be desired or as necessary to achieve the goals of the particular test specified.

A medium to facilitate growth of the target microorganism is preferably placed in each of target compartments 126 prior to final assembly of test device 100. Depending on the test being performed, different media may be utilized to detect different microorganisms. It is also envision that the device of this invention can be used or configured to detect any detectable analytes, for example chemical analytes, such as total chlorine, free chlorine, nitrate, fluoride, phosphorus, in the liquefied sample for water chemistry analysis. The powder chemical reactants may be dispensed in metered amounts directly into each of target compartments 126 such that the medium immediately dissolves in the sample when the sample is poured into test device 100. In some instances it may be desirable to conduct parallel tests in different compartments or groups of compartments. This process is also referred to as multiplexing.

The choice of testing medium will depend on the biological material to be detected. The testing medium preferably detects the presence/absence of the biological material and preferably does not detect the presence of other biological material likely to be in the medium. It should be a material, which will cause some visible or otherwise sensible change, such as color change or fluorescence, if the biological material sought to be detected is present in the sample. In one embodiment, the medium is in a powder form to simplify the overall manufacturing process. Additionally, use of a powdered medium greatly enhances the medium stability and provides a greater shelf life for the assembled test devices 100. The powder may be dispensed in metered amounts directly into each of target compartments 126 such that the medium immediately dissolves in the sample when the sample is poured into test device 100. In one preferred embodiment, beads such as glass beads, silica gel beads, or metal beads are added along with the powder medium to target compartments 126 allowing rapid dissolution of the powder by shaking the assembled test device 100 upon sample introduction into the device.

In alternative embodiments, other rapid medium dispersion methods may be utilized, for example, a porous solid-containment material may be utilized to form medium retention and dispersion bags (not shown) which may be inserted individually in however many of the target compartments 126 is desired. It is also contemplated that dispersion bags containing different media for performing different tests can be placed in the same test device 100 in different test compartments 126 to facilitate multiplex testing. The medium dispersion bags function in an analogous manner to that of a tea bag, wherein the material of the bag is porous to permit flow-through of fluids. However, the size of the pores formed in the material making up the bags is preferably sized to retain the medium until dissolved by the fluid sample. Still other rapid medium dispersion devices and techniques are envisioned, for example, quick dissolve tablets, water-permutable seals, etc. In each of the above-noted medium placement embodiments, the medium forms an integrated part of the device as shipped, thereby eliminating the need for a separate medium package and the separate step of preparing the medium. However, such separate packaging is an option contemplated herein.

A sealable cap such as threaded cap 124 and gasket 122 are provided to form a seal between at the open end of each target chamber 126 with respect to the outside environment and with respect to each of the other target chambers 126. Gasket 122 is preferably a hydrophobic material, such as a non-absorbent, closed cell foam gasket material. In this manner, a sealed test environment is provided. Further, cross-contamination (cross-talk) between the individual target compartments 126 is prevented. Alternatively, if only venting of gas is desired such as to vent any pressure build up from an exothermic reaction, then the vent holes could be configured as bleeder valve openings permitting the built up gas pressure to escape while preventing the introduction of ambient air into the target chambers 126.

An optional fill ring collar 120 is secured to the top end of container 112 by suitable attachment techniques, for example, friction fit, ultrasonic welding, bonding, adhesives, etc. Fill ring collar 120 includes an overflow channel formed around the periphery thereof to receive and contain excess sample which may spill over after target chambers 126 become filled.

In one illustrative method of using test device 100, cap 124 and the gasket 122 retained therein are removed. Seal 118 is peeled away and 100 ml of sample is poured in and diverted to each of the target chambers by way of fill diverter 116. Alternatively, the sample could be metered in by way of a pipette array. No sample pre-treatment is required for the embodiment wherein the active media is pre-dispensed and dried down within the target chambers. The sample fills, equally metered, to each of the wells, where it re-hydrates the media and mixes therewith to achieve a proper sample/medium mixture. Alternatively, the sample can be mixed with the test medium forming a sample/medium mixture before its introduction into the device.

Threaded cap 124, containing a non-absorbent, closed cell foam gasket 122, is then returned to the outer vessel. Gasket 122 is thereby compressed to contact the top of container 112. This action seals each target chamber 126 from the remaining compartments and the outside environment. During this action gasket 122 also direct any excess sample into overflow channel 122a, which is designed and placed in a manner to isolate the excess volume from the array of test compartments 126. This internal isolation action prevents any of the individual test reactions from being cross contaminated by sample from any of the other test compartments 126.

Test device 100 is then incubated or left at room temperature for the required duration as indicated by the particular test protocol to develop the result (preferably a color-metric change, viewable by the unaided eye). These positive indications are then counted. The device may be incubated either right side up or upside down. Additionally, the device may be re-opened, via the threaded cap, allowing further sub-culturing of individual isolates, which may develop during the test period.

Upon completion of the test, the device may be disposed of under proper methods. The device platform also allows for "multiplexing" of different medium types, i.e., permitting a number of tests to be performed simultaneously.

An alternative method is also envisioned wherein no gasket is required. In this embodiment, a lid (not shown) may be provided to facilitate distribution of the sample and individually sealing each of the test compartments from the adjacent chambers.

Figure 9:
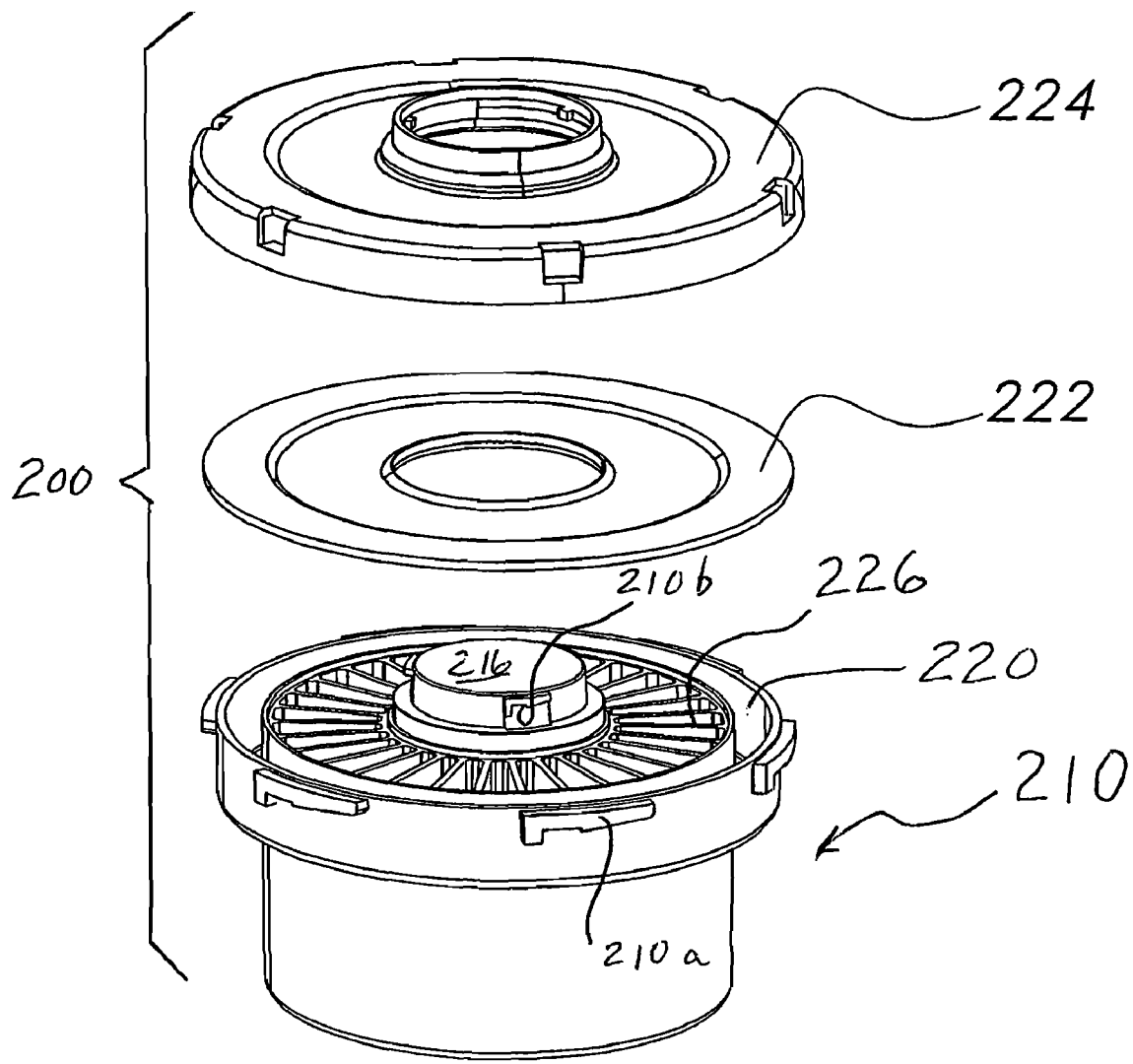
FIG. 9 is a perspective view with parts separated from a slightly angled and top orientated perspective of an alternative one-piece design which incorporates the features of multiple components into a single unit; and incorporates the functions of the embodiment of FIG. 1.

Referring to FIG. 9, a further alternative embodiment of the presently disclosed liquid sample testing apparatus is shown as test device 200. Instead of the multiple components which form the sub-assembly of the multi-compartmented chamber 110 of the test device 100 as shown in FIG. 3, test device 200 includes a unitary chamber 210 which incorporate the features of multiple components into a single unit for example by way of injection molding.

A sealable cap such as cap 224 and gasket 222 are provided to form a seal between at the open end of each target chamber 226 with respect to the outside environment and with respect to each of the other target chambers 226. Gasket 222 is preferably a hydrophobic material, such as a non-absorbent, closed cell foam gasket material to provide a sealed test environment and prevent cross-contamination between target chambers 226. Cap 224 is removably secured to chamber 210, for example by bayonet style catches 210a and 210b formed around the periphery of fill ring collar 220 and fill diverter 216, respectively. Alternative removable securing methods are also envisioned, such as, threaded engagement.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A method for quantification of biological material in a liquefied sample, comprising the steps of:
   a) providing a device having a reaction chamber enclosing a volume therein, said reaction chamber having an upper opening through which a liquefied sample can be poured and a plurality of discrete non-permeable compartments, each of said compartments having an upper rim and being configured and dimensioned to hold separate aliquots of a liquefied sample therein; a diverter defining an upper surface having an edge portion disposed in direct contact with the upper rims of the plurality of compartments, the diverter disposed in fluid communication with the upper opening; and a gasket lid removably secured to the top of said device, said gasket lid being configured and dimensioned for sealing the upper rim of each compartment to prevent liquid communication between said compartments;
   b) pouring a liquefied sample through the upper opening of to said device such that the liquefied sample is diverted to fill each of the compartments;
   c) securing the gasket lid on top of said device thereby sealing said compartments; and
   d) detecting the presence or absence of said biological material in each of said compartment.

2. The method of claim 1, wherein a testing medium is provided for detecting the presence or absence of said biological material in each of said compartments.

3. The method of claim 2, wherein the biological material to be quantified is selected from one or more bacterial species and the testing medium is a specific biological detection medium.

4. The method of claim 3, wherein said one or more bacterial species is *Escherichia coli* and coliform bacteria.

5. The method of claim 3, wherein the specific biological detection medium is a medium for detecting enterococci bacteria in a sample.

6. The method of claim 3, wherein the specific biological detection medium is pre-dispensed into the compartments.

7. The method of claim 3, wherein the specific biological detection medium is mixed with the liquefied sample prior to distribution into the device.

8. The method of claim 3, wherein the specific biological detection medium comprises two or more distinct media that are individually distributed in different compartments, thereby providing multiplex detection.

9. The method of claim 1, wherein the number of compartments is between 12 and 36.

10. The method of claim 1, wherein the compartments are of substantially equal size.

11. The method of claim 1, wherein the compartments are configured and dimensioned to hold about four milliliters of liquid.

12. The method of claim 1, wherein the compartments are of trapezoidal cross-section shape.

13. The method of claim 1, wherein the compartments are arranged in a circular fashion within the device.

14. The method of claim 1, wherein the compartments comprise a first plurality of compartments of one size and a second plurality of compartments of a different size than the first size.

15. The method of claim 1, wherein the compartments comprise a third plurality of compartments of a size different from said first and second plurality of compartments.

16. The method of claim 1, wherein the liquefied sample is water.

17. The method of claim 1, wherein the device is formed at least partially from polystyrene.

18. The method of claim 1, wherein the gasket lid has both internal and external bayonet style closures.

* * * * *